US012156925B2

(12) United States Patent
De La Poterie et al.

(10) Patent No.: US 12,156,925 B2
(45) Date of Patent: Dec. 3, 2024

(54) COSMETIC COMPOSITIONS COMPRISING ANHYDROUS SPHEROIDS DISPERSED IN A SILICONE PHASE

(71) Applicant: LVMH RECHERCHE, Saint Jean de Braye (FR)

(72) Inventors: Valérie De La Poterie, Lailly en Val (FR); Sabrina Maniguet, Trainou (FR); Armelle Masanelli, Tigy (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 16/957,007

(22) PCT Filed: Dec. 20, 2018

(86) PCT No.: PCT/FR2018/053462
§ 371 (c)(1),
(2) Date: Jun. 22, 2020

(87) PCT Pub. No.: WO2019/122754
PCT Pub. Date: Jun. 27, 2019

(65) Prior Publication Data
US 2020/0330335 A1    Oct. 22, 2020

(30) Foreign Application Priority Data

Dec. 22, 2017  (FR) ...................... 1763086

(51) Int. Cl.
*A61K 8/02*        (2006.01)
*A61K 8/25*        (2006.01)
(Continued)

(52) U.S. Cl.
CPC ............. *A61K 8/025* (2013.01); *A61K 8/25* (2013.01); *A61K 8/891* (2013.01); *A61K 8/92* (2013.01);
(Continued)

(58) Field of Classification Search
CPC ............ A61K 2800/31; A61K 2800/41; A61K 2800/652; A61K 8/025; A61K 8/25; A61K 8/31; A61K 8/89; A61K 8/891; A61K 8/92; A61K 8/987; A61K 8/14; A61K 8/678; A61K 8/733; A61K 8/11; A61K 8/55; A61K 8/553; A61K 8/042; A61K 9/1617; A61K 2800/56; A61K 8/585; A61K 8/0279; A61K 8/06; A61K 8/375; A61K 8/39; A61K 2800/262; A61K 2800/43; A61K 47/02; A61K 47/06; A61K 8/0229; A61K 8/04; A61K 8/28; A61K 8/365; A61K 8/42; A61K 8/442; A61K 8/4933; A61K 8/8111; A61K 8/8117; A61K 8/922; A61K 9/0014; A61K 9/06; A61K 9/1694; A61K 2300/00; A61K 31/192; A61K 31/196; A61K 9/0019; A61K 9/0024; A61K 9/1647; A61K 2800/412; A61K 2800/413; A61K 47/14; A61K 47/26; A61K 8/0216; A61K 8/0241; A61K 8/062; A61K 8/361; A61K 8/37; A61K 8/60; A61K 31/28; A61K 31/43; A61K 8/8123; A61K 8/8141; A61K 31/353; A61K 41/0057; A61K 9/5161; A61K 9/7053; A61K 31/17; A61K 31/4402; A61K 8/8135; A61K 47/186; A61K 31/505; A61K 35/60; A61K 2039/55566; A61K 31/498; A61K 47/28; A61K 9/0051; A61K 9/7015; A61K 2800/756951; A61K 2800/59; A61K 8/4913; A61K 8/555; A61K 31/59; A61K 31/26; A61K 2800/524; A61K 2800/4893; A61K 48/00; A61K 48/4174; A61K 33/14; A61K 33/497; A61K 31/4985; A61K 8/496; A61K 2800/49; A61K 31/138; A61K 9/2072; A61K 31/675; A61K 9/5052; A61K 31/23; A61K 2800/60; A61K 31/35; A61K 8/604; A61K 8/897; A61K 31/10;
(Continued)

(56) References Cited

U.S. PATENT DOCUMENTS 5,532,000 A    7/1996   Kauffmann
5,556,613 A    9/1996   Arnaud et al.
(Continued)

FOREIGN PATENT DOCUMENTS

CN    104379217 A     2/2015
EP    0452202         10/1991
(Continued)

OTHER PUBLICATIONS

EP0665008A1 translation, Jan. 1995, Arnaud et al., "Arnaud II". (Year: 1995).*
(Continued)

*Primary Examiner* — Audrea B Coniglio
(74) *Attorney, Agent, or Firm* — HSML P.C.

(57) ABSTRACT

The invention relates to an anhydrous cosmetic composition comprising anhydrous spheroids having a diameter of 0.1 to 10 mm and having a melting point above 50° C., said spheroids consisting of a cosmetically acceptable lipid matrix, solid at room temperature, comprising:
  (a) at least one hydrocarbon oil, and optionally a gelling agent for said hydrocarbon oil, and/or
  (b) at least one wax, said spheroids being dispersed in an immiscible continuous phase comprising at least one silicone oil.
More specifically, this cosmetic composition can be a lipstick or a foundation.

19 Claims, No Drawings

(51) Int. Cl.
  *A61K 8/891* (2006.01)
  *A61K 8/92* (2006.01)
  *A61K 8/98* (2006.01)
  *A61Q 1/06* (2006.01)

(52) U.S. Cl.
  CPC .............. *A61K 8/987* (2013.01); *A61Q 1/06* (2013.01); *A61K 2800/652* (2013.01)

(58) Field of Classification Search
  CPC .............. A61K 31/255; A61K 2800/34; A61K 31/336; A61K 8/0275; A61K 8/645; A61K 9/5138; A61K 2800/42; A61K 35/745; A61K 36/28; A61K 2800/882; A61K 31/34; A61K 31/715; A61K 33/06; A61K 9/2063; A61K 2800/438015; A61K 31/351; A61K 38/19; A61K 9/0036; A61K 9/1688; A61K 31/569; A61K 31/7042; A61K 8/97; A61K 31/517; A61K 38/4833; A61K 47/60; A61K 2039/543; A61K 2800/91; A61K 31/444; A61K 31/5383; A61K 36/53; A61K 38/28; A61K 47/54; A61K 8/8194; A61K 33/22; A61K 38/1709; A61K 9/148; A61K 31/232; A61K 31/538; A61K 31/5517; A61K 31/02; A61K 31/035; A61K 31/136; A61K 31/27; A61K 31/397; A61K 31/421; A61K 31/424; A61K 31/7084; A61K 31/731; A61K 31/732; A61K 31/77; A61K 35/64; A61K 36/064; A61K 36/14; A61K 36/17; A61K 36/254; A61K 36/286; A61K 36/324; A61K 36/36; A61K 36/41; A61K 36/54; A61K 36/736; A61K 36/8998; A61K 38/005; A61K 38/15; A61K 38/1732; A61K 38/217; A61K 38/33; A61K 38/34; A61K 38/443; A61K 38/46; A61K 38/57; A61K 39/001186; A61K 39/015; A61K 39/39558; A61K 41/0071; A61K 47/52; A61K 47/547; A61K 47/593; A61K 47/6925; A61K 49/0021; A61K 49/0438; A61K 51/083; A61K 51/088; A61K 8/0262; A61K 8/30; A61K 8/9741; A61K 8/986; A61K 9/0041; A61K 9/0097; A61K 9/204; A61K 2035/128; A61K 2039/515; A61K 2039/585; A61K 2039/6031; A61K 2039/625; A61K 2236/31; A61K 2800/4322; A61K 2800/542; A61K 31/055; A61K 31/06; A61K 31/275; A61K 31/4245; A61K 31/4468; A61K 31/45; A61K 31/527; A61K 31/541; A61K 31/609; A61K 31/658; A61K 31/717; A61K 31/726; A61K 31/736; A61K 31/738; A61K 31/745; A61K 31/795; A61K 33/02; A61K 35/02; A61K 35/08; A61K 35/20; A61K 35/37; A61K 35/57; A61K 35/612; A61K 35/646; A61K 35/655; A61K 35/748; A61K 36/03; A61K 36/15; A61K 36/234; A61K 36/235; A61K 36/25; A61K 36/288; A61K 36/37; A61K 36/489; A61K 36/515; A61K 36/535; A61K 36/739; A61K 36/758; A61K 36/808; A61K 36/882; A61K 36/888; A61K 36/896; A61K 38/018; A61K 38/04; A61K 38/1751; A61K 38/1891; A61K 38/191; A61K 38/208; A61K 38/2086; A61K 38/24; A61K 38/385; A61K 38/4806; A61K 38/50; A61K 38/52; A61K 39/00115; A61K 39/001156; A61K 39/001164; A61K 39/001191; A61K 39/001192; A61K 39/02; A61K 47/557; A61K 47/61; A61K 47/643; A61K 47/665; A61K 47/6835; A61K 49/0008; A61K 49/0056; A61K 49/0082; A61K 49/0091; A61K 49/0423; A61K 49/0442; A61K 49/085; A61K 49/126; A61K 49/14; A61K 49/223; A61K 6/17; A61K 6/30; A61K 6/54; A61K 6/69; A61K 8/418; A61K 8/9778; A61K 9/0092; A61K 9/2036; A61K 9/5094; A61K 2035/115; A61K 2035/124; A61K 2039/55577; A61K 2039/6025; A61K 2236/11; A61K 2236/19; A61K 2236/35; A61K 2236/50; A61K 2236/53; A61K 31/105; A61K 31/132; A61K 31/133; A61K 31/221; A61K 31/315; A61K 31/382; A61K 31/4425; A61K 31/4453; A61K 31/4523; A61K 31/4525; A61K 31/536; A61K 31/549; A61K 31/5578; A61K 31/625; A61K 31/6615; A61K 31/662; A61K 31/7072; A61K 31/718; A61K 31/719; A61K 31/737; A61K 33/32; A61K 35/19; A61K 35/24; A61K 35/38; A61K 35/39; A61Q 1/02; A61Q 1/04; A61Q 1/06; A61Q 19/08; A61Q 13/00; A61Q 19/00; A61Q 19/10; A61Q 1/14; A61Q 11/00; A61Q 15/00; A61Q 19/001; A61Q 1/10; A61Q 5/006; A61P 29/00

See application file for complete search history.

(56) References Cited

U.S. PATENT DOCUMENTS

| | | | |
|---|---|---|---|
| 5,569,465 A | 10/1996 | Kauffmann | |
| 5,674,504 A | 10/1997 | Kauffmann | |
| 5,750,095 A * | 5/1998 | Arnaud | A61Q 1/06 424/64 |
| 6,572,892 B1 * | 6/2003 | Ioulalen | A61K 9/0014 424/400 |
| 6,843,982 B1 | 1/2005 | Arnaud et al. | |
| 9,114,076 B2 * | 8/2015 | Dumousseaux | A61K 8/0279 |
| 2002/0159961 A1 | 10/2002 | Yamato et al. | |
| 2004/0223937 A1 | 11/2004 | Arnaud et al. | |

FOREIGN PATENT DOCUMENTS

| | | | | |
|---|---|---|---|---|
| EP | 0452202 A1 * | 10/1991 | | A61K 8/025 |
| EP | 0462709 | 12/1991 | | |
| EP | 0665008 A1 * | 1/1995 | | A61K 7/48 |
| EP | 0665008 | 8/1995 | | |
| FR | 2649608 | 1/1991 | | |
| FR | 2779962 | 12/1999 | | |
| FR | 2779962 A1 * | 12/1999 | | A61K 9/48 |
| FR | 2820739 | 8/2002 | | |
| JP | 2005336119 A | 12/2005 | | |
| JP | 2007238578 A | 9/2007 | | |
| JP | 2009274975 A | 11/2009 | | |
| JP | 2015506357 A | 3/2015 | | |

(56) References Cited

FOREIGN PATENT DOCUMENTS

WO      2013102065 A1    7/2013
WO      2013190129 A1    12/2013

OTHER PUBLICATIONS

EP0452202A1 translation (Year: 1991).*
MINTEL Record ID: 4228439, Date Published: Oct. 2016, Parfums Christian Dior: "Ultra-Gloss" (5 pages).
MINTEL Record ID: 3263269, Date Published: Jun. 2015, Parfums Christian Dior: "Lipstick" (5 pages).
MINTEL Record ID: 5206147, Date Published: Nov. 2017, Parfums Christian Dior: "Jewel Lipstick Couture Colour Comfort & Wear" (5 pages).
MINTEL Record ID: 4395479, Date Published: Dec. 2016, Parfums Christian Dior: "Mat Velvet Colour Lipstick" (5 pages).
MINTEL Record ID: 4601379, Date Published: Feb. 2017, Make-Up Art Cosmetics: "Matte Lipstick" (4 pages).
International Search Report and Written Opinion issued for International Patent Application No. PCT/FR2018/053462, Date of mailing: Apr. 3, 2019, 14 pages including English translation of Search Report.
Search Report issued for French Application No. 1763086, dated Jul. 20, 2018, 3 pages.

* cited by examiner

COSMETIC COMPOSITIONS COMPRISING ANHYDROUS SPHEROIDS DISPERSED IN A SILICONE PHASE

The invention relates to a cosmetic composition comprising anhydrous spheroids dispersed in an immiscible continuous phase comprising at least one silicone oil. More particularly, this cosmetic composition may be a lipstick or a foundation.

PRIOR ART AND PURPOSE OF THE INVENTION

The cosmetics industry has always been searching for compositions that produce surprising effects. These can be compositions with an original visual appearance, for example by dispersing solid particles of different colors in a transparent continuous phase. They can also be new compositions that combine performances that are difficult to associate using traditional techniques, such as freshness and shine, freshness and hold, shine and hold.

However, obtaining stable compositions by association of immiscible phases is not an easy task, as incompatibility between phases poses stability problems.

In the case of emulsions combining two liquid phases, the skilled person will try to prevent the globules of the dispersed phase from merging, and thus leading to a separation of the phases, for example by using surfactants to stabilize the droplets.

In the case of dispersions of visible solid particles in a liquid or gelled continuous phase, the solid particles are often either dispersed or suspended in the continuous phase. It is particularly important to avoid gradual diffusion of the continuous phase into the solid particles or, conversely, diffusion of the material constituting the solid particles into the continuous phase. This is particularly problematic when the continuous phase is translucent or transparent, as any diffusion of material into the continuous phase is then immediately visible.

A first problem underlying the present invention thus consists in obtaining a stable anhydrous composition in the form of solid spheroids dispersed in a continuous phase, in which the spheroids are sufficiently hard at room temperature to retain their shape and integrity, do not deform, and do not release material in said continuous phase immiscible with said spheroids.

A second problem underlying the invention is to obtain a biphasic composition in which the spheroids have a sufficiently flexible structure to be easily crushed and applied to the skin by a slight shearing or crushing movement, for example using a finger. The spheroids can thus be easily mixed with the continuous phase to form a single phase at the time of application, for example on the skin or lips, and thus combine the properties of the two phases.

Compositions comprising spheroids in a continuous phase have already been described in the prior art.

FR 2 649 608 describes for example a composition comprising a continuous phase in the form of an aqueous gel containing, suspended in said continuous phase, lipid spheroids having an average diameter of between 50 and 10 000 μm and having a melting point below 50° C. The low-melting point spheroids have insufficient hardness which affects both their shape (polydisperse and non-homogeneous spheroids) and the stability of the final composition.

The Inventors observed that anhydrous cosmetic compositions comprising spheroids consisting of a lipid matrix with a melting point above 50° C., dispersed in a continuous phase comprising at least one silicone oil, can solve the above problems in a quite surprising manner.

Unexpectedly, they also showed that high-melting point spheroids have good spreading properties. Thus, the anhydrous compositions of the invention are very easy to apply and produce a surprising texture when applied to the skin, the spheroids and the immiscible continuous phase in which they are dispersed mixing in situ to accentuate a sensory and/or color performance, such as a property of shine (gloss), hold, sensory stimulation or comfort on the surface of the skin. It is possible to observe the transformation of the compositions according to the invention from gel to cream and/or the transformation of a mixture of spheroids of different colors with the continuous phase into a single uniform shade, while producing a surprising sensory effect due to the simultaneous contact of these two immiscible phases with the skin.

To date, no anhydrous compositions have ever been proposed whose immiscible phases solve the above-mentioned problems.

DESCRIPTION OF THE INVENTION

According to a first aspect, the subject matter of the present invention is an anhydrous cosmetic composition comprising anhydrous spheroids having a diameter of 0.1 to 10 mm and having a melting point above 50° C., said spheroids consisting of a cosmetically acceptable lipid matrix comprising:
  (a) at least one hydrocarbon oil, and optionally a gelling agent for said hydrocarbon oil, and/or
  (b) at least one wax,
said spheroids being dispersed in an immiscible continuous phase comprising at least one silicone oil.

For the purposes of the invention, "lipid matrix" means a homogeneous composition (i.e. not comprising a coating layer around a core) based on fatty substances, i.e. comprising (a) at least one hydrocarbon oil, and/or (b) at least one wax.

For the purposes of the invention, the expression "immiscible" means that the spheroids of the invention do not diffuse, disintegrate or swell in the phase in which they are dispersed.

For the purposes of the invention, the term "spheroid" refers to a small solid of essentially spherical shape, solid at room temperature, having the same composition throughout the spheroid. Room temperature means a temperature between 15 and 27° C., and more generally between 20 and 25° C. The diameter of the spheroids may vary from 0.1 to 10 mm, preferably from 0.3 to 8 mm, more preferentially from 0.5 to 5 mm, and even more preferentially from 1 to 3 mm, this diameter being an average diameter measured over ten measurements by conventional methods, for example using a binocular magnifying glass or a sieve. These spheroids preferably have a regular appearance, a smooth surface and a uniform volume.

Advantageously, the spheroids of the invention are free of any external coating designed to isolate the lipid matrix from the external medium (i.e. the continuous phase), having a composition different from that of the lipid matrix.

The term "anhydrous" means, in the context of the invention, that the water content of the object in question is preferably less than 1% by weight, and even more preferentially less than 0.5% by weight, of said object.

The spheroids of the invention consist of a lipid matrix whose texture, at room temperature, is sufficiently supple and deformable to be easily applied to the skin with low shear, for example with the fingers, and thus produce a skin care or make-up effect on the skin.

The Inventors observed that the nature of the constituents used in the composition of the spheroids of the invention may have an influence not only on the ease of application of these spheroids, but also on their final properties.

Thus, according to an advantageous embodiment, the hydrocarbon oil (a) is selected from volatile and/or non-volatile hydrocarbon oils. It is preferably a mixture of hydrocarbon oils.

The hydrocarbon oil(s) (a), and optionally the gelling agent for said hydrocarbon oil, may be present in a content ranging from 5 to 99.5% by weight, preferably from 10 to 95% by weight, more preferentially from 20 to 90% by weight, even more preferentially from 30 to 85% by weight, and even more preferentially from 40 to 80% by weight, relative to the total weight of the lipid matrix.

For the purposes of the invention, "hydrocarbon oil" means an oil containing mainly carbon and hydrogen atoms, and possibly atoms of oxygen, nitrogen, sulfur and phosphorus.

A volatile hydrocarbon oil as defined in the invention is an oil capable of evaporating on contact with the skin in less than one hour at room temperature and atmospheric pressure. The volatile oil or oils of the invention are oils which are liquid at room temperature, having a vapor pressure which is not zero, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg). Non-volatile hydrocarbon oil means an oil remaining on the skin at room temperature and atmospheric pressure for at least several hours and in particular having a vapor pressure of less than 0.13 Pa ($10^{-3}$ mmHg).

The volatile hydrocarbon oils of the invention are advantageously selected from hydrocarbon oils having from 8 to 16 carbon atoms, and in particular branched alkanes containing from 8 to 16 carbon atoms such as isoalkanes containing from 8 to 16 carbon atoms (also called isoparaffins) of petroleum origin such as isododecane (also called 2,2,4,4,6-pentamethylheptane), isodecane, isohexadecane, and for example oils sold under the trade names Isopar™ or Permetyls (ExxonMobil Chemical), branched esters with 8 to 16 carbon atoms such as iso-hexyl neopentanoate, and mixtures thereof. Other volatile hydrocarbon oils such as petroleum distillates, including those sold as Shell Solt by SHELL, may also be used. The volatile hydrocarbon oils may also be selected from linear alkanes with 8 to 16 carbon atoms. Examples of linear alkanes with 8 to 16 carbon atoms are n-nonadecane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$), n-hexadecane ($C_{16}$), and mixtures thereof, and in particular the mixture of n-undecane ($C_{11}$) and n-tridecane ($C_{13}$) sold as CETIOL UT by Cognis.

According to an embodiment, a volatile linear alkane suitable for the invention may be selected from n-nonadecane, n-undecane, n-dodecane, n-tridecane, and mixtures thereof.

The volatile hydrocarbon oils of the invention are advantageously selected from volatile hydrocarbon oils having 8 to 16 carbon atoms, and mixtures thereof.

As non-volatile hydrocarbon oils, particular mention may be made to: hydrocarbon oils of vegetable origin such as triesters of fatty acids and glycerol including fatty acids containing from 4 to 24 carbon atoms, these oils may be linear or branched, saturated or unsaturated. These oils are advantageously wheat germ, sunflower, grape seed, sesame, corn, apricot, castor, shea, avocado, olive, soya, sweet almond, palm, rapeseed and cottonseed oils, hazelnut, macadamia, jojoba, alfalfa, poppy, pumpkin, sesame, squash, rapeseed, blackcurrant, evening primrose, millet, barley, quinoa, rye, safflower, bancoulier, passionflower, muscat rose; or caprylic/capric acid triglycerides such as those sold by Stéarineries Dubois or those sold as Miglyol® 810, 812, 818 and 829 by Dynamit Nobel; or linear or branched hydrocarbons with 4 to 24 carbon atoms, of mineral or synthetic origin such as petroleum jelly, polydecenes, hydrogenated polyisobutene such as Parleam®, squalane, and mixtures thereof; synthetic esters such as for example Purcellin™ (ketostearyl octanoate) oil, isopropyl myristate, isopropyl palmitate, alcohol benzoate with 12 to 15 carbon atoms, hexyl laurate, diisopropyl adipate, isononyl isononanoate, 2-ethyl-hexyl palmitate, isostearyl isostearate, octanoates, decanoates or ricinoleates of alcohols or polyalcohols such as propylene glycol dioctanoate; hydroxyl esters such as isostearyl lactate, di-isostearyl malate; and esters of pentaerythritol; fatty alcohols which are liquid at room temperature with a branched and/or unsaturated carbon chain with 12 to 26 carbon atoms such as octyl dodecanol, isostearyl alcohol, oleic alcohol, 2-hexyldecanol, 2-butyloctanol, 2-undecylpentadecanol; higher fatty acids such as oleic acid, linoleic acid, linolenic acid; carbonates, acetals, citrates, and mixtures thereof.

When the lipid matrix of the invention does not comprise wax (b), the hydrocarbon oil or oils (a) are combined with at least one gelling agent for said hydrocarbon oils.

The gelling agent for the hydrocarbon oil is preferably selected from silicas, clays, optionally modified hectorites, dextrin esters, polyamides or silicone polyamides, amides of L-glutamic acid or aspartic acid, hydrocarbon block copolymers comprising at least one styrene unit.

For the purposes of the invention, the hectorites may be hectorites modified by a quaternary alkylammonium chloride, preferably an ammonium substituted by at least one, preferably at least two alkyl groups with 14 to 20 carbon atoms. The alkyl may advantageously be stearyl. Mention may be made of the compound bearing the INCI name disteardimonium hectorite in which the ammonium comprises two methyl groups and two stearyl groups.

For the purposes of the invention, dextrin esters are esters of dextrin and fatty acids containing 12 to 24 carbon atoms, preferably containing 14 to 22 carbon atoms and even more preferentially containing 14 to 18 carbon atoms. Preferably the dextrin esters are selected from dextrin myristate, dextrin palmitate, and mixtures thereof.

For the purposes of the invention, the amides of L-glutamic acid (glutamides) or aspartic acid preferably comprise at least one alkyl group containing from 6 to 14 carbon atoms, for example 8 or 12 carbon atoms. Such an amide of glutamic acid is for example described in patent FR 2 820 739. Glutamides are preferably selected from dibutyl lauroyl glutamide, dibutyl ethylhexanoyl glutamide, and mixtures thereof, and may be for example one of the branded products EB-21, GP-1, AJK-OD2046, AJK-BG2055 and AJK-CE2046 manufactured by Ajinomoto. Glutamide is for example selected from dibutyl lauroyl glutamide and dibutyl ethylhexanoyl glutamide, or mixtures thereof.

The amide or mixture of amides, in particular glutamide (s), represents for example between 0.1% and 15.0% by weight, between 1.0% and 15.0% by weight, between 0.5% and 8.0% by weight, between 1.0% and 5.0% by weight, between 0.8% and 5% by weight or between 2.0 and 3.0% by weight relative to the total weight of the lipid matrix.

For the purposes of the invention, hydrocarbon block copolymers comprising at least one styrene unit are preferably block copolymers of styrene and olefin, such as, for example, copolymers comprising at least one styrene unit and a unit selected from butadiene, ethylene, propylene, butylene, isoprene and mixtures thereof. The hydrocarbon block copolymers of the invention are advantageously selected from styrene-ethylene/propylene copolymers, styrene-ethylene/propylene-styrene copolymers, styrene-ethylene/butadiene-styrene copolymers, styrene-isoprene-styrene copolymers, styrene-butadiene-styrene copolymers, styrene-ethylene/butylene-styrene copolymers, styrene/methylstyrene/indene copolymers, and mixtures thereof.

The wax or waxes (b) used in the context of the invention may be a lipophilic compound, solid at room temperature, with a reversible solid/liquid change of state, having a melting temperature above 30° C., preferably from 50 to 120° C., more preferentially from 60 to 110° C., and even more preferentially from 70 to 100° C. For the purposes of the invention, the melting temperature corresponds to the temperature of the most endothermic peak observed in thermal analysis (DSC) as described in standard NF EN ISO 11357-3. The melting temperature of wax can be measured using a differential scanning calorimeter (DSC), for example the calorimeter sold as DSC Mettler Toledo.

Wax mixtures can advantageously be formed by combining waxes with a high melting temperature, i.e. with a melting temperature above 50° C., preferably above 70° C., with waxes with lower melting temperatures, i.e. with a melting temperature below 50° C., preferably below or equal to 40° C. The mixture of waxes having a high melting temperature with waxes having a low melting temperature must make it possible to obtain spheroids having a melting point higher than 50° C.

The spheroids of the invention can advantageously be characterized by a melting point (or dropping point) ranging from 50 to 120° C., more preferentially from 60 to 110° C.; and even more preferentially from 70 to 100° C. The melting point of the lipid matrix corresponds to the temperature at which the first drop of lipid matrix appears when the latter is heated.

The wax or waxes (b) used in the context of the invention may be selected from waxes solid at room temperature of animal, vegetable, mineral or synthetic origin, and mixtures thereof.

Advantageously, the wax or waxes (b) of the invention may be selected from:

hydrocarbon waxes such as beeswax, lanolin wax, Chinese insect waxes, rice bran wax, Carnauba wax, Candelilla wax, Ouricury wax, Alfa wax, cork fiber wax, sugar cane wax, berry wax, shellac wax, Japan wax, sumac wax, montan wax, orange and lemon waxes, paraffin waxes and ozokerite, polymethylene waxes, polyethylene waxes, polypropylene and their ethylene/propylene copolymers, the waxes obtained by catalytic hydrogenation of animal or vegetable oils having fatty chains, linear or branched, with 8 to 22 carbon atoms, such as isomerized jojoba oil, hydrogenated sunflower oil, hydrogenated castor oil, hydrogenated coconut oil, hydrogenated lanolin oil, di-(trimethylol-1,1,1-propane) tetrastearate and di-(trimethylol-1,1,1-propane) tetra behenate;

fatty alcohol waxes selected from saturated or unsaturated, linear or branched fatty alcohols with 20 to 60 carbon atoms, silicone waxes, such as alkyl- or alkoxy-dimethicones with 16 to 45 carbon atoms, or fluorinated waxes, and mixtures thereof.

According to a particularly advantageous embodiment, the wax or waxes (b) are apolar waxes, preferably selected from hydrocarbon waxes such as Microcrystalline Wax SP-88 and Microcrystalline Wax SP-16 W (Strahl and Pitsch Inc.), and/or polyethylene waxes such as Jeenate® (Jeen International Corporation) and Performalene® (Baker Hughes), hydrocarbon waxes being the most preferred. The hydrocarbon waxes of the invention are advantageously waxes containing from 18 to 60 carbon atoms.

The content of wax(es) (b) may vary from 0.5 to 95% by weight, preferably from 3 to 90% by weight, more preferentially from 3 to 60% by weight, even more preferentially from 4 to 45% by weight, and even more preferentially from 5 to 30% by weight, relative to the total weight of the lipid matrix constituting the anhydrous spheroids of the invention.

The anhydrous spheroids of the invention may also comprise at least one pigment or nacre (mother-of-pearl), preferably an organic or inorganic pigment. The pigment or nacre of the invention may have been surface-treated, i.e. have undergone one or more surface treatments of a chemical, electronic, mechanochemical and/or mechanical nature.

The pigment or nacre content advantageously varies from 0 to 20% by weight, and preferably from 2 to 10% by weight, relative to the total weight of the lipid matrix.

The continuous phase of the composition of the invention, immiscible with anhydrous spheroids, comprises at least one volatile and/or non-volatile silicone oil.

Volatile silicones, such as, for example, volatile linear or cyclic silicone oils, in particular with 2 to 7 silicon atoms, these silicones optionally containing alkyl or alkoxy groups with 1 to 10 carbon atoms, can be mentioned as volatile silicone oils. As volatile silicone oils usable in the context of the invention, preferential mention may be made of cyclopentadimethylsiloxane, octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane, dodecamethyl pentasiloxane, and mixtures thereof.

Mention may also be made of the linear volatile alkyltrisiloxane oils selected from 3-butyl-1,1,1,3,5,5,5-heptamethyl trisiloxane, 3-propyl-1,1,1,3,5,5,5-heptamethyl trisiloxane, and 3-ethyl-1,1,1,3,5,5,5-heptamethyl trisiloxane, and mixtures thereof.

The preferred volatile silicone oil is cyclopentadimethylsiloxane.

The non-volatile silicone oils usable in the composition according to the invention may be polydimethylsiloxanes (PDMS) comprising at least one alkyl or alkoxy group advantageously with 12 to 24 carbon atoms, during and/or at the end of the silicone chain, phenylated silicones such as phenyl trimethicones, phenyl dimethicones, phenyl trimethylsiloxy diphenylsiloxanes, diphenyl dimethicones, diphenyl methyl diphenyl trisiloxanes, 2-phenylethyl tri methylsiloxysilicates.

The continuous phase may also include a fluorinated oil selected from fluorosilicone oils, fluoropolyethers, and fluorosilicones. Volatile fluorinated oils such as nonafluoromethoxybutane or perfluoromethylcyclopentane may be used.

According to a preferred embodiment, the continuous phase is gelled by at least one silicone oil gelling agent. The gelling agent for the silicone oil may be selected from fumed silicas, clays, optionally modified hectorites, dextrin esters, glycerol esters and polyamides. Advantageously, the gelling agent is selected from fumed silica and silica aerogel particles. Fumed silica is chemically modified at the surface by chemical reaction to generate a decrease in the number of silanol groups present on the surface of the silica. In particular, the silanol groups can be replaced by hydrophobic groups such as:

trimethylsiloxyl groups, which are obtained in particular by treatment of fumed silica in the presence of hexamethyldisilazane. Silicas treated in this way are called "silica silylate" according to the CTFA (8th edition, 2000). For example, they are marketed as Aerosil R812® by EVONIK INDUSTRIES, dimethylsilyloxyl or polydimethylsiloxane groups, which are obtained in particular by treatment of fumed silica in the presence of polydimethylsiloxane or dimethyldichlorosilane. Silicas treated in this way are referred to as "silica dimethyl silylate" according to the CTFA ($8^{th}$ edition, 2000). They are for example marketed as Aerosil R972® and Aerosil R974® by EVONIK INDUSTRIES.

The use of the gelling agent for the silicone oil makes it possible to obtain a continuous gelled phase. The continuous gelled phase is preferably translucent or transparent. The term "translucent" means that the continuous phase allows light rays to pass through diffusely, without allowing the contours of the spheroids contained in it to be clearly distinguished. The term "transparent" means that the continuous phase allows light to pass through by refraction, which makes it possible to clearly distinguish the spheroids it contains. This property of transparency is particularly sought-after when dispersing colored spheroids in the siliconized continuous phase, which results in a very attractive visual effect.

The continuous phase can also advantageously comprise a silicone elastomer, preferably previously dispersed in silicone oil. The silicone elastomer is generally in the form of a gel, a paste, or a powder, advantageously in the form of a gel in which the silicone elastomer is dispersed in a hydrocarbon oil and/or a silicone oil. The silicone elastomer is advantageously selected from polydimethylsiloxane (PDMS) (or dimethicone), methyl-polysiloxane (MQ), vinyl-methyl-polysiloxane (VMQ), phenyl-vinyl-methyl-polysiloxane (PVMQ), fluoro-vinyl-methyl-polysiloxane (FVMQ), and mixtures thereof. Specifically, these include gels KSG-15 and KSG-16, marketed by Shin-Etsu Silicone, DC 9040 and DC 9041, marketed by Dow Corning, and Gransil PC-12, marketed by Grant Industries, Inc.

The continuous phase may include a film-forming polymer. A film-forming polymer is defined as a polymer capable of forming a continuous film on a substrate. The film-forming polymer can be of natural or synthetic origin, and is advantageously selected from:

tri methylsiloxysilicates, phenylalkylsiloxysilicates in which the alkyl group preferably comprises 1 to 6 carbon atoms, such as phenylpropyldimethylsiloxysilicate, silicone acrylate polymers such as acrylate/dimethicone copolymers, in particular acrylate/dimethicone copolymers in cyclopentasiloxane (such as KP-545 from Shin-Etsu), acrylate/dimethicone copolymers in methyl trimethicone (for example KP-579 from Shin-Etsu), acrylate/dimethicone copolymers in isododecane (for example KP-550 from Shin-Etsu); acrylate/polytrimethylsiloxy-methacrylate copolymers, in particular acrylate/polytrimethylsiloxy-methacrylate copolymers in dimethicone (for example FA-4003 DM from Dow Corning®), acrylate/polytrimethylsiloxy-methacrylate copolymers in isododecane (for example FA-4004 ID from Dow Corning®), polyalkylsilsesquioxanes with 1 to 6 carbon atoms, preferably polymethylsilsesquioxane (such as Silform® Flexible Resin from Momentive), trialkylsiloxysilylcarbamoyl pullulans in which the alkyl group comprises 1 to 6 carbon atoms, and preferably trimethylsiloxysilylcarbamoyl pullulan (such as TSPL-30-ID from Shin-Etsu), copolymers of vinylpyrrolidone (VP), and preferably copolymers of VP and alkene with 2 to 20 carbon atoms, such as copolymers of VP/eicosene, VP/vinyl acetate, VP/ethyl methacrylate, VP/ethyl methacrylate/ methacrylic acid, VP/hexadecene, VP/triacontane, VP/styrene, VP/acrylic acid/lauryl methacrylate, butylated polyvinylpyrrolidone (PVP), copolymers of a vinyl ester, and preferably vinyl acetate/ allyl stearate, vinyl acetate/vinyl laurate, vinyl acetate/ vinyl stearate, vinyl acetate/octadecene, vinyl acetate/ octadecyl vinyl ether, vinyl propionate/allyl laurate, vinyl propionate/vinyl laurate, vinyl stearate/octadecene-1, vinyl acetate/dodecene-1, vinyl stearate/ethyl vinyl ether, vinyl propionate/cetyl vinyl ether, vinyl stearate/allyl acetate, vinyl dimethyl-2,2-octanoate/vinyl laurate, allyl dimethyl-2,2-pentanoate/vinyl laurate, vinyl dimethyl propionate/vinyl stearate, allyl dimethyl propionate/vinyl stearate, polyolefins, hydrogenated or non-hydrogenated, and preferably polymers or copolymers of alkenes with 2 to 20 carbon atoms, such as polybutenes, polyisobutenes, polydecenes, alkylcelluloses, and preferably alkylcelluloses carrying an alkyl group with 2 to 6 carbon atoms, such as ethylcellulose and propylcellulose, polyvinyl alcohols, and mixtures thereof.

The film-forming polymer is preferably selected from silicone polymers such as trimethylsiloxysilicates; phenylalkylsiloxysilicates in which the alkyl group preferably comprises from 1 to 6 carbon atoms such as phenylpropyldimethylsiloxysilicate; and copolymers of vinylpyrrolidone.

Depending on the intended end application, the anhydrous cosmetic composition of the invention may also contain additives usual in the cosmetic field, such as fillers or preservatives.

The fillers can be mineral or organic, and of any shape, platelet, spherical or oblong.

The fillers are selected in particular from inorganic fillers such as talc, micas of natural or synthetic origin, kaolin, metallic soaps derived from organic carboxylic acids with 8 to 22 carbon atoms, and preferably with 12 to 18 carbon atoms, for example zinc stearate, magnesium stearate or lithium stearate, zinc laurate, magnesium myristate, zinc oxides, titanium oxides, calcium carbonate, magnesium carbonate, magnesium hydrocarbonate, glass beads, ceramic beads, and mixtures thereof.

Organic fillers such as cross-linked or uncross-linked starches, synthetic polymer powders, cross-linked or uncross-linked, spheronized or not, expanded or not, such as polyethylene powders, polyester powders (for example isophthalate or terephthalate), polyamide powders (for example poly-β-alanine powders and nylon powders such as those marketed as ORGASOM, poly(meth)acrylic acid or poly(meth)acylate powders such as cross-linked methyl methacrylate powders, polyurethane powders such as copolymers of hexamethylene diisocyanate and trimethylol hexyl lactone sold as PLASTIC POWDER® D-400 and PLASTIC POWDER® D-800 by TOSHIKI, divinylbenzene-cross-linked polystyrene powders, silicone resin powders such as silsesquioxanes, or tetrafluoroethylene (Teflon®) powders, and mixtures thereof can also be used as fillers.

In the cosmetic composition of the invention, the proportion by weight of anhydrous spheroids may represent from 5 to 70% by weight, preferably from 10 to 60% by weight, and even more preferentially from 20 to 50% by weight, relative to the total weight of the cosmetic composition.

The second object of the invention relates to a process for preparing a cosmetic composition according to the invention comprising the following steps:
(i) a step of preparing a lipid matrix constituting the anhydrous spheroids of the invention by homogenizing at least one hydrocarbon oil (a) and optionally a gelling agent for said hydrocarbon oil, and/or at least one wax (b), with stirring, at a temperature ranging from 50 to 120° C., in order to obtain a liquid and totally molten mixture,
(ii) a step of shaping the liquid mixture obtained in step (i) by dispersion, with stirring, in an aqueous phase heated to a temperature ranging from 50 to 120° C.,
(iii) a step of sudden cooling of the dispersion obtained in step (ii), by adding an aqueous phase preferably having a temperature less than or equal to 0° C., to solidify the droplets obtained in step (ii) and to obtain spheroids,
(iv) a step of separating by filtration the spheroids obtained in step (iii), at room temperature, for example using a molecular sieve,
(v) a step of drying the spheroids obtained in step (iv), preferably at room temperature, to remove residual water,
(vi) a step of dispersing the spheroids obtained in step (v), with stirring, in a continuous phase comprising at least one silicone oil.

The continuous phase comprising at least one silicone oil can be gelled by adding a gelling agent for the silicone oil, before or after the step of dispersing the spheroids in the continuous phase. The continuous phase is then heated to a temperature of 50 to 120° C., preferably to a temperature of 85° C., and the gelling agent is incorporated into the silicone oil with stirring. Once the continuous phase has been homogenized (absence of grains), it is cooled to room temperature.

The third object of the invention relates to the use of a cosmetic composition according to the invention for make-up and/or care of the skin of the body or face, and in particular the lips.

The invention also relates to a lipstick and a foundation comprising a cosmetic composition according to the invention.

Finally, a last object of the invention relates to a make-up and/or skin care process for the body or face, and in particular the lips, comprising the following steps:
(i') collecting a quantity of cosmetic composition according to the invention, in the quantity necessary to carry out at least one application,
(ii') shear mixing the anhydrous spheroids with the immiscible continuous phase comprising at least one silicone oil, contained in the cosmetic composition of the invention, and
(iii') applying the cosmetic composition thus mixed to the skin of the body or face, in particular the lips.

The mixing step by shearing can be carried out either directly on the skin of the body or face (direct application), for example using the fingers, or beforehand, within a dispensing device such as a package containing the cosmetic composition of the invention (indirect application). In the latter case, the texture of the cosmetic composition may be dispensed in the form of spheroids which are then crushed during application or modified into a cream or gel within said dispensing device, before application to the skin.

In addition to the foregoing provisions, the invention includes further provisions which will be apparent from the following additional description, which relates to the preparation of cosmetic compositions according to the invention.

EXAMPLES

The different tests and measurement methods used in the examples are as follows:
Measurement of the Average Diameter of the Spheroids:
24 hours after manufacture, a dozen spheroids are taken. Their diameters are measured with a binocular magnifying glass at ×10 magnification at room temperature. The mean diameter of the spheroids represents the average of these ten measurements.
Melting Point Measurement:
During the preparation of the lipid matrix, a sample of this matrix is poured into a pierced reservoir. This reservoir is maintained at 20° C., under atmospheric pressure, for 24 hours. It is then placed in an oven and heated at a heating rate of 1° C. per minute. The melting point corresponds to the melting of the first drop of lipid matrix in the reservoir.
Stability Test:
Stability is evaluated at different temperatures: at 4° C., at room temperature, and in the oven at 50° C., for a period of one month.

Example 1

Preparation of a Lipstick Composition Comprising Anhydrous Spheroids in a Continuous Silicone Phase:

TABLE 1

Composition of the spheroids (Composition 1)

| Chemical name | Trade name (supplier) | % by weight |
|---|---|---|
| Polyglyceryl-2-triisostearate | Salacos 43V (Nisshin Oillio Group) | 17.5 |
| Hydrogenated polyisobutene | Parleam ® (NOF Corporation) | 12.4 |
| Hydrogenated poly-1-decene | Dekanex 2006 FG (IMCD France) | 11.3 |
| Disteardimonium hectorite | Bentone Gel ® PTIS V (Elementis Specialties) | 8.8 |
| Synthetic wax | Lipwax A-4 (Ina Trading) | 7.4 |
| Trimethylolpropane triisostearate | Salacos 6318V (Nisshin Oillio Group) | 6.6 |
| Hydrogenated methyl rosinate | Floralyn (PFW Aroma Chemicals) | 6.0 |
| Polybutene | Polybutene M100 (Kemat) | 6.0 |
| Ozokerite | Permulgin 3233 (Koster Keunen) | 4.0 |
| Jojoba ester | Floraester ® 30 (Floratech) | 2.7 |
| Polyethylene wax | Jeenate 3H (Jeen International Corporation) | 2.0 |
| Beeswax | Cerabeil blanchie DAB (Baerlocher) | 2.0 |

TABLE 1-continued

Composition of the spheroids (Composition 1)

| Chemical name | Trade name (supplier) | % by weight |
|---|---|---|
| Fillers | | 2.0 |
| Pigments | | 10.0 |
| Nacre | | 1.2 |
| Antioxidant | | 0.1 |
| TOTAL: | | 100.0 |

All the ingredients of composition 1 are heated to 85° C., with stirring, until a homogeneous mixture is obtained. The mixture thus obtained is then slowly dispersed in water at 85° C., while maintaining stirring, until droplets are obtained. The dispersion obtained is then cooled abruptly by adding an aqueous phase at 0° C. Stirring is stopped to avoid damaging the solidified spheroids. The spheroids are then separated by filtration and dried at room temperature.

Characterization of the Spheroids Obtained:
  Melting point: 81° C.,
  Average diameter: 2.5 mm.

TABLE 2

Composition of the silicone continuous phase (Composition 2)

| Chemical Name | Trade name (supplier) | % by weight |
|---|---|---|
| Diphenyl dimethicone | KF-54HV (Shin-Etsu) | 80.7 |
| Polydimethylsiloxane and acrylate/polytrimethyl-siloxy-methacrylate copolymer | Dow Corning ® FA 4003 DM (Dow Corning) | 12.5 |
| VP/eicosene copolymer | Unimer U15 (Givaudan Active Beauty) | 5.0 |
| Silica | Aerosil 200 (Evonik Industries) | 1.8 |
| TOTAL: | | 100.0 |

The continuous silicone phase of composition 2 is prepared by mixing the various components listed in Table 2. Diphenyl dimethicone (silicone oil) is heated to a temperature of 85° C., and then silica (gelling agent) is gently added to the silicone oil. The mixture is then kept under vigorous stirring at a temperature of 85° C. until a homogeneous (grain-free) mixture is obtained. The two polymers are then added while hot, at a temperature of 85° C., and the mixture is homogenized by stirring. The mixture is then cooled to room temperature until a translucent gel is obtained.

The previously prepared spheroids of composition 1 are then dispersed in the continuous silicone phase of composition 2 in a composition 1/composition 2 weight ratio of 40/60, with stirring, at room temperature.

Evaluation of the Properties of the Lipstick Composition:

Gloss Test:

Gloss is measured by polarimetric imaging. The test consists of manually spreading a precise quantity of the composition (0.15 g) on a synthetic skin, Bio Skin Plate, over an area of 170×30 mm. The composition is spread in a strip of homogeneous thickness to obtain a smooth surface. Three strips are thus prepared. For each measurement, the Bio Skin Plate sample is placed on the cylindrical holder of a SAMBA Hair device in order to visualize the sample. Three gloss measurements are performed on each strip at different locations.

The gloss values obtained are shown in Table 3 below, with the results expressed in gloss units:

TABLE 3

| Measures | Reference gloss | Reference gloss lipstick | Reference satin lipstick | Reference matte lipstick | Composition of the invention |
|---|---|---|---|---|---|
| Mean | 38.8 | 37.0 | 16.9 | 10.1 | 41.4 |
| Standard deviation | 1.16 | 0.08 | 0.05 | 0.02 | 1.10 |

Reference gloss: product DIOR ADDICT ULTRA-GLOSS (Mintel ID: 4228439)
Reference gloss lipstick: product DIOR ADDICT LIPSTICK (Mintel ID: 3263269)
Reference satin lipstick: product ROUGE DIOR INTERNATIONAL (Mintel ID: 5206147)
Reference matte lipstick: product DIORIFIC (Mintel ID: 4395479)

The composition of the invention has a higher level of gloss than that of reference lipsticks, and even higher than that of a gloss.

Sensory Test:

A comparative sensory test between a lipstick according to the invention (anhydrous spheroids of composition 1 in a continuous silicone phase of composition 2) and a reference long-lasting matte lipstick (MAC MAT LIPSTICK, Russian Red shade, Mintel ID: 4601379) is then carried out on a panel of eight subjects.

Lipsticks are evaluated according to different criteria: glide, gloss, comfort, migration and transfer after 3 hours, gloss and film hold after 3 hours, according to a rating scale ranging from 0 (poor) to 4 (excellent).

TABLE 4

| Properties evaluated | Reference long-lasting matte lipstick | Lipstick according to the invention |
|---|---|---|
| Glide | 2 | 3 |
| Gloss | 1 | 4 |
| Comfort | 3 | 3 |
| Migration (after 3 h) | 1 | 1 |
| Transfer (after 3 h) | 2 | 2 |
| Gloss retention (after 3 h) | 0 | 3 |
| Film holding (after 3 h) | 2 | 2 |

The lipstick of the invention has a level of performance equivalent to the reference long-lasting matte lipstick in terms of migration, transfer and film hold, while exhibiting superior gliding power, gloss and gloss hold.

Example 2

Four anhydrous spheroid compositions A, B, C and D are prepared.

The spheroids of compositions A and B correspond to the spheroids in application FR 2 649 608. They have a low melting point of 36-38° C. A pigment has been added to enhance the visualization of these spheroids.

The compositions A, B, C and D are as follows:

TABLE 5

Composition A

| Chemical name | Trade name (supplier) | % by weight |
|---|---|---|
| Hemisynthetic triglycerides | Lipocire A tablets (Gattefosse) | 99.0 |
| Castor oil | | 0.8 |
| Pigment | | 0.2 |
| TOTAL: | | 100.0 |

TABLE 6

Composition B

| Chemical name | Trade name (supplier) | % by weight |
|---|---|---|
| Olive oil ester | Phytowax olive 10L 40 (Sophim) | 99.0 |
| Castor oil | | 0.8 |
| Pigment | | 0.2 |
| TOTAL: | | 100.0 |

TABLE 7

Composition C

| Chemical name | Trade name (supplier) | % by weight |
|---|---|---|
| Polyethylene wax | Performalene 500 (Baker Hughes) | 7.2 |
| Beeswax | Cerabeil blanchie dab (Univar) | 1.4 |
| Microcrystalline | Microcrystalline wax sp 16 wp (Rossow) | 3.6 |
| Dilinoleyl-dilinoleate dimer | Lusplan DD-DA7 (Unipex) | 7.0 |
| Hydrogenated methyl rosinate | Floralyn new process (Safic Alcan) | 20.0 |
| Hydrogenated olive oil, unsaponified | Exolive wax SR (Caroi'Line) | 5.0 |
| Polyisobutene | Parleam ® (Rossow) | 10.0 |
| Octyldodecanol | Isofol 20 (IMCD France) | 8.0 |
| Polyglyceryl-2-triisostearate | | 24.05 |
| Antioxidant | | 0.1 |
| Fillers | | 0.5 |
| Pigment | | 12.9 |
| Fragrances | | 0.25 |
| TOTAL: | | 100.0 |

Composition C consists of 69.05% non-volatile oils (a) (of which 10% is apolar oil) and 17.2% waxes (b).

TABLE 8

Composition D

| Chemical name | Trade name (supplier) | % by weight |
|---|---|---|
| Beeswax | Candelilla wax sp 75G (Rossow) | 10.0 |
| Rice wax | Rice wax no 1 (Saci/CFPA) | 1.5 |
| Hexadecyl 12-hydroxyoctadec-9-enoate | Cetyl ricinoleate (Laboratoires PROD HYG) | 2.0 |
| Caprylic/Capric/Succinic Triglyceride | Miglyol 829 MB (IMCD France) | 4.0 |
| 2,6,10,15,19,23-Hexamethyltetracosane | Vegetable squalane (Perhydrosqualene) | 10.0 |
| Diisostearyl malate | Salacos 222 (Saci/CFPA) | 8.0 |
| C$_{10-30}$ cholesterol/lanosterol esters | Super sterol ester (Croda) | 3.0 |
| Mixture of propylene carbonate, stearalkonium hectorite and castor oil | Bentone Gel CAO V (Saci/CFPA) | 5.0 |
| Beeswax | Cerabeil blanchie dab (Univar) | 2.6 |
| Ozokerite | Cerozo G 168 (Univar) | 0.5 |
| Castor oil | | 29.0 |
| Octyl methoxycinnamate | | 3.0 |
| Antioxidant | | 1.0 |
| Fillers | | 2.0 |
| Pigment | | 17.5 |
| Fragrances | | 0.9 |
| TOTAL: | | 100.0 |

Composition D consists of 57% oils (a) and 19.6% waxes (b).

Spheroids of composition A, B, C and D were prepared by the same process:
  The ingredients are heated, mixed and homogenized at 50° C. for compositions A and B, and at 80° C. for compositions C and D,
  When the mixture is homogeneous, it is slowly dispersed in an aqueous phase heated to the same temperature. Stirring is maintained until droplets are obtained.
  The mixture is then cooled abruptly by adding an aqueous phase cooled to 0° C. Stirring is stopped to avoid damaging the solidified spheroids.
  The spheroids are then filtered and dried at room temperature.
  The spheroids are then incorporated into a continuous silicone phase of composition H, in a ratio by weight of anhydrous spheroids to composition H of 40/60, with stirring at room temperature.

TABLE 9

Composition of the silicone continuous phase (Composition H)

| Chemical name | Trade name (supplier) | % by weight |
|---|---|---|
| Diphenyl dimethicone | KF-54HV (Shin-Etsu) | 97.0 |
| Silica | Aerosil 200 (Evonik Industries) | 3.0 |
| TOTAL: | | 100.0 |

The silicone continuous phase is prepared by heating diphenyl dimethicone (silicone oil) to a temperature of 85° C. and then gently adding silica (gelling agent) to the silicone oil. The mixture is then kept under strong stirring at a temperature of 85° C., until a homogeneous (grain-free) mixture is obtained.

Characterization of the Spheroids Obtained:

The anhydrous spheroids of composition A, B, C and D obtained are then characterized according to the tests described above. The results are shown in Table 10 below.

TABLE 10

| | Melting point | Average diameter of the spheroids (mm) | Appearance of the spheroids | Stability |
|---|---|---|---|---|
| Composition A | 37.7° C. | 1.7 | Spherical spheroids | Poor |
| Composition B | 42.5° C. | 1.9 | Rods | Poor |
| Composition C | 71.9° C. | 2.1 | Spherical spheroids | Good |
| Composition D | 68.1° C. | 2.0 | Spherical spheroids | Good |

The spheroids of composition A and B have a melting point below 50° C. and are not stable over time. On the other hand, the handling of the spheroids during their incorporation into the silicone continuous phase is very tricky: the spheroids have lost their shape and agglomerate in clusters, which makes it very difficult to incorporate them into the silicone continuous phase. In addition, the spheroids obtained are not regular and have more elongated, non-reproducible shapes.

The spheroids of composition C and D, which have a melting point above 50° C., retain their shape and size after one month in the oven. They are easy to handle and incorporate into the continuous silicone phase. In addition, the spheroids of composition C and D show good stability over time. Unlike the spheroids of composition A and B, they are easily incorporated into the continuous silicone phase with moderate stirring and do not agglomerate with each other.

Example 3

Preparation of a Lipstick Composition According to the Invention Comprising Anhydrous Spheroids in a Continuous Silicone Phase:

TABLE 11

Composition of the spheroids (Composition E)

| Chemical name | Trade name (supplier) | % by weight |
|---|---|---|
| Beeswax | Super refined Beeswax PA (Croda) | 8.0 |
| Stearyl heptanoate-Stearyl caprylate | PCL Solid (Symrise) | 15.0 |
| Beeswax | Cerabeil Blanchie dab (Baerlocher) | 1.4 |
| Rice wax | Rice wax no 1 (Saci/CFPA) | 3.0 |
| Hexadecyl 12-hydroxy-octadec-9-enoate | Cetyl Ricinoleate (PROD HYG Laboratories) | 2.0 |
| Capyrlic/capric/succinic triglyceride | Miglyol 829 MB (IMCD France) | 4.0 |
| 2,6,10,15,19,23-Hexamethyltetracosane | Vegetable squalane (Perhydrosqualene) | 6.0 |
| Diisostearyl malate | Salacos 222 (Saci/CFPA) | 6.0 |

TABLE 11-continued

Composition of the spheroids (Composition E)

| Chemical name | Trade name (supplier) | % by weight |
|---|---|---|
| $C_{10-30}$ cholesterol/lanosterol esters | Super sterol ester (Croda) | 2.5 |
| Mixture of propylene carbonate, stearalkonium hectorite and castor oil | Bentone Gel CAD V (Saci/CFPA) | 4.0 |
| Azacyclotridecan-2-one | Orgasol ® 2002 D NAT COS (Arkema) | 1.0 |
| Calcium aluminum borosilicate | Ronaflake (MERCK) | 8.0 |
| Nacre | Sunshine Fine white C80-3100 (maprecos) | 5.0 |
| VP/eicosene copolymer | Unimer U15 (Givaudan Active Beauty) | 5.0 |
| Pigments | | 25.0 |
| Octyl methoxycinnamate | | 3.0 |
| Antioxidant | | 0.2 |
| Fragrances | | 0.9 |
| TOTAL: | | 100.0 |

All the ingredients of composition E are heated to 85° C., with stirring, until a homogeneous mixture is obtained. The mixture thus obtained is then slowly dispersed in water at 85° C., while maintaining stirring, until droplets are obtained. The dispersion obtained is then suddenly cooled by adding an aqueous phase cooled to 0° C. Stirring is stopped to avoid damaging the solidified spheroids. The spheroids are then separated by filtration and dried at room temperature.

Characterization of the Spheroids Obtained:
  Melting point: 68.1° C.,
  Average diameter: 2.1 mm.

TABLE 12

Composition of the silicone continuous phase (Composition F)

| Chemical name | Trade name (supplier) | % by weight |
|---|---|---|
| Diphenyl dimethicone | KF-54HV (Shin-Etsu) | 76.1 |
| Silica | Aerosil 200 (Evonik Industries) | 3.0 |
| Decamethylcyclo-pentasiloxane | Volatile pentacyclo-methicone | 10.0 |
| Cyclopentasiloxane | KF-7312 J (Shin Etsu Chemical Co) | 7.0 |
| Hexadecene copolymer | Unimer U-151 (Givaudan Assets) | 3.9 |
| TOTAL: | | 100.0 |

The silicone continuous phase of composition F is prepared by mixing the various ingredients listed in Table 12.

Diphenyl dimethicone (silicone oil) is heated to a temperature of 85° C., then silica (gelling agent) is gently added to the silicone oil. The mixture is then kept under strong stirring at a temperature of 85° C. until a homogeneous mixture (without grains) is obtained. The other ingredients are then added while hot, at a temperature of 85° C., and the mixture is homogenized by stirring. The mixture is then cooled to room temperature until a translucent gel is obtained.

The previously prepared spheroids of composition E are then dispersed in the silicone continuous phase of composition F, in a weight ratio composition E/composition F of 40/60, with stirring, at room temperature.

Preparation of a Comparative Lipstick Composition G Comprising a Mixture of Compositions E and F:

The cosmetic composition of the invention based on spheroids of composition E dispersed in a continuous silicone phase of composition F is compared with a comparative cosmetic composition G in which the previously described compositions E and F are mixed in proportions composition E/composition F of 40/60.

To prepare the comparative cosmetic composition G, all the ingredients of compositions E and F are heated to 85° C., with stirring, until a homogeneous mixture is obtained. The mixture is then cooled, with stirring, to room temperature.

Evaluation of the Properties of the Two Final Lipstick Compositions:

Stability Test:

Stability is assessed using the test described above. After one month, the comparative cosmetic composition G has a granular appearance with an oily layer on the surface. In contrast, the appearance of the cosmetic composition of the invention is not modified: the spheroids remain dispersed in the silicone continuous phase, and the shape of the spheroids is not affected.

Gloss Test:

Gloss is measured using a Micro-gloss S gloss-meter from BYK Additives and Instruments. The two cosmetic compositions were spread with a shearing bar on a contrast card, with a film thickness of 40 μm and a spreading speed of 4 m/sec. After a drying time of 15 minutes at room temperature, ten measurements were performed on the entire card.

The gloss values are shown in Table 13 below, with the results expressed in gloss units:

TABLE 13

|  | Cosmetic composition of the invention | Cosmetic composition G |
|---|---|---|
| Mean | 65.1 | 56.45 |
| Standard deviation | 1.1 | 0.35 |

The cosmetic composition according to the invention comprising spheroids of composition E dispersed in a continuous silicone phase of composition F has a higher level of gloss than the comparative cosmetic composition G.

Sensory Test:

A comparative sensory test between the cosmetic composition according to the invention and the comparative cosmetic composition G was conducted on a panel of ten subjects. Each subject applied each composition with an identical number of passages and answered a questionnaire in order to evaluate the product's shine and hold.

The two compositions were evaluated according to different criteria: shine, stickiness on application, shine and hold after 3 hours, according to the rating scale shown in Table 14:

TABLE 14

| Note | Shine | Stickiness | Hold |
|---|---|---|---|
| 0 | Does not shine | Does not stick | No hold |
| 1 | Shines moderately | Slightly sticky | Poor hold |

TABLE 14-continued

| Note | Shine | Stickiness | Hold |
|---|---|---|---|
| 2 | Shines | Moderately sticky | Average hold |
| 3 | Good shine | Sticky | Good hold |
| 4 | Mirror shine | Very sticky | Very good hold |

The results are set out in Table 15 below:

TABLE 15

|  | Cosmetic composition of the invention | Comparative cosmetic composition G |
|---|---|---|
| Shine | 4 | 2 |
| Sticky at application | 2 | 2 |
| Shine (after 3 h) | 2 | 1 |
| Hold (after 3 h) | 3 | 2 |

The cosmetic composition of the invention globally presents a higher level of performance than the comparative cosmetic composition G.

The invention claimed is:

1. An anhydrous cosmetic composition, which comprises anhydrous spheroids having a diameter of 0.1 to 10 mm and having a melting point above 70° C. said anhydrous spheroids consisting of a cosmetically acceptable lipid matrix which is solid at room temperature and comprising:
   (a) at least one hydrocarbon oil with a gelling agent for said hydrocarbon oil, and
   (b) at least one wax,
   wherein a content of wax(es) varies from 5 to 30% by weight,
   said anhydrous spheroids being dispersed in an immiscible continuous phase comprising at least one silicone oil,
   said gelling agent for said hydrocarbon oil being selected from the group consisting of hectorites, modified hectorites, dextrin esters, silicone polyamides, polyamides, amides of L-glutamic acid, amides of aspartic acid, and hydrocarbon block copolymers comprising at least one styrene unit, and
   said anhydrous spheroids not diffusing, disintegrating or swelling in the continuous phase in which they are dispersed, and
   said anhydrous spheroids representing from 20 to 50% by weight relative to a total weight of the cosmetic composition.

2. The cosmetic composition as claimed in claim 1 wherein said spheroids are free of any external coating.

3. The cosmetic composition as claimed in claim 1, wherein the hydrocarbon oil (a) is selected from the group consisting of a volatile hydrocarbon oil, a non-volatile hydrocarbon oil or a mixture of a volatile hydrocarbon oil and a non-volatile hydrocarbon oil.

4. The cosmetic composition as claimed in claim 1, wherein said at least one wax (b) is selected from the group consisting of hydrocarbon waxes, polyethylene waxes, and mixture thereof.

5. The cosmetic composition as claimed in claim 1, wherein said lipid matrix further comprises at least one of a pigment and a mother-of-pearl.

6. The cosmetic composition as claimed in claim 1, wherein said continuous phase comprising at least one silicone oil is gelled by the gelling agent to form a continuous gelled phase.

7. A process for manufacturing a cosmetic composition as claimed in claim 1, which comprises the following steps:
(i) a step of preparing a lipid matrix constituting the anhydrous spheroids by homogenizing at least one hydrocarbon oil (a) with a gelling agent for said hydrocarbon oil, and at least one wax (b), with stirring, at a temperature above 70° C.,
(ii) a step of shaping the liquid mixture obtained in step (i) by dispersion, with stirring, in an aqueous phase heated to a temperature ranging from above 70° C.,
(iii) a step of cooling the dispersion obtained in step (ii) by adding an aqueous phase, to obtain spheroids,
(iv) a step of separating by filtration the spheroids obtained in step (iii), at room temperature,
(v) a step of drying the spheroids obtained in step (iv),
(vi) a step of dispersing the spheroids obtained in step (v), with stirring, in a continuous phase comprising at least one silicone oil,
wherein said spheroids do not diffuse, disintegrate, or swell in the continuous phase in which they are dispersed,
wherein a content of wax(es) varies from 5 to 30% by weight and said anhydrous spheroids representing from 20 to 50% by weight relative to a total weight of the cosmetic composition.

8. A lipstick which comprises a cosmetic composition as claimed in claim 1.

9. A foundation which comprises a cosmetic composition as claimed in claim 1.

10. A process for make-up or care of the skin of the body or face, which comprises the following steps:
(i') collecting a quantity of the cosmetic composition as claimed in claim 1, in a quantity necessary to carry out at least one application,
(ii') shear mixing the anhydrous spheroids with the immiscible continuous phase comprising at least one silicone oil, and
(iii') applying the cosmetic composition thus mixed to the skin of the body or face,
wherein said anhydrous spheroids do not diffuse, disintegrate, or swell in the continuous phase in which they are dispersed.

11. The process as claimed in claim 10, wherein the shear mixing step is carried out either directly on the skin of the body or face or prior to application to the skin of the body or face, within a dispensing device containing said cosmetic composition.

12. The cosmetic composition as claimed in claim 1, wherein said at least one wax (b) is selected from the group consisting of hydrocarbon waxes.

13. The cosmetic composition as claimed in claim 1, wherein said lipid matrix further comprises at least one pigment selected from the group consisting of an organic pigment and an inorganic pigment.

14. The cosmetic composition as claimed in claim 1, wherein the hydrocarbon oil (a) is selected from the group consisting of a volatile hydrocarbon oil, a non-volatile hydrocarbon oil or a mixture of a volatile hydrocarbon oil and a non-volatile hydrocarbon oil.

15. The cosmetic composition as claimed in claim 1, wherein the hydrocarbon oil (a) is selected from the group consisting of a volatile hydrocarbon oil, a non-volatile hydrocarbon oil or a mixture of a volatile hydrocarbon oil and a non-volatile hydrocarbon oil; and said at least one wax (b) is selected from the group consisting of hydrocarbon waxes, polyethylene waxes, and mixture thereof.

16. The cosmetic composition as claimed in claim 1, wherein said spheroids have a melting point ranging between 7° and 120° C.

17. The cosmetic composition as claimed in claim 16, wherein said spheroids have a melting point ranging between 7° and 100° C.

18. The cosmetic composition as claimed in claim 1, wherein the cosmetic composition is configured such that the anhydrous spheroids have a flexible structure in the immiscible continuous phase such that the anhydrous spheroids are able to be crushed and applied by a shearing or crushing movement to form a single phase during application.

19. The cosmetic composition as claimed in claim 18, wherein the anhydrous cosmetic composition is configured such that during the formation of the single phase during application, the anhydrous cosmetic composition has a transformation of the composition due at least in part to a mixing of the anhydrous spheroids with the immiscible continuous phase.

* * * * *